United States Patent [19]

Parsons et al.

[11] 4,451,648

[45] May 29, 1984

[54] PROCESS FOR THE PRODUCTION OF 2-β-D-RIBOFURANOSYLTHIAZOLE-4-CARBOXAMIDE

[75] Inventors: Jack L. Parsons, East Aurora; Dan Vizine, Tonawanda, both of N.Y.; Mark Sumner, Chatham, N.J.; Suresh Marathe, Tonawanda, N.Y.; Henryk Dubicki, Lancaster, N.Y.

[73] Assignee: The United States of America as represented by the Department of Health and Human Services, Washington, D.C.

[21] Appl. No.: 294,368

[22] Filed: Aug. 19, 1981

[51] Int. Cl.³ ............... C07G 37/00; C07H 37/00; C08B 37/00
[52] U.S. Cl. ............................................. 536/54
[58] Field of Search .......................... 536/23, 548

[56] References Cited

U.S. PATENT DOCUMENTS

| | | | |
|---|---|---|---|
| Re. 29,835 | 11/1978 | Witkowski et al. | 536/29 |
| 1,684,732 | 9/1938 | Harrison | 536/54 |
| 3,798,209 | 3/1974 | Witkowski et al. | 536/23 |
| 3,897,415 | 7/1975 | Robins et al. | 536/23 |
| 3,927,216 | 12/1975 | Witkowski et al. | 424/269 |
| 3,976,545 | 8/1976 | Witkowski et al. | 195/28 N |
| 4,138,547 | 2/1979 | Christensen et al. | 536/23 |
| 4,211,771 | 7/1980 | Witkowski et al. | 424/180 |

OTHER PUBLICATIONS

Srivastava et al., Journ. Med. Chem. 20,256 (1977).
Chem. Abstracts 97:145235t (1982).
Fuertes et al., J. Org. Chem. 41(26), p. 4074 (1976).

Primary Examiner—Ethyl G. Love
Attorney, Agent, or Firm—John S. Roberts, Jr.

[57] ABSTRACT

An improved multi-step process for the production of 2-β-D-ribofuranosylthiazole-4-carboxamide.

8 Claims, No Drawings

PROCESS FOR THE PRODUCTION OF 2-β-D-RIBOFURANOSYLTHIAZOLE-4-CARBOXAMIDE

The invention described herein was made in the course of work under a grant or award from the Department of Health and Human Services.

The present invention is directed to a new and unique multi-step process for the production of 2-β-D-ribofuranosylthiazole-4-carboxamide, which is known in the literature as an antiviral agent.

The procedure for the multi-step process is given as follows:

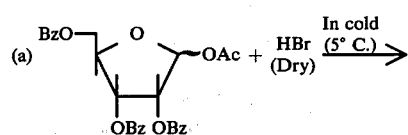

Tri-O—benzoyl-α-acetyl-D-ribofuranose

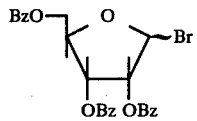

(I)

2,3,5-Tri-O—benzoyl-D-ribofuranosyl bromide

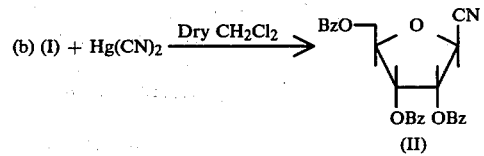

(II)

2,3,5-Tri-O—benzoyl-β-D-ribofuranosyl cyanide

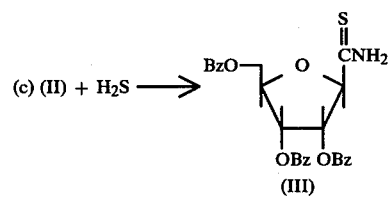

(III)

2,5-Anhydro-3,4,6-tri-O—benzoyl-D-allonthioamide

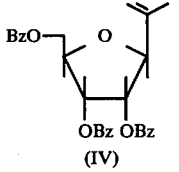

(IV)

Thiazole-4-carboxylic acid, 2-(2',3',5'-tri-O—benzoyl-β-D-ribofuranosyl)-, ethyl ester

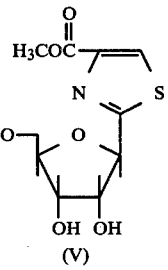

(V)

2-β-D-ribofuranosylthiazole-4-carboxylic acid, methyl ester

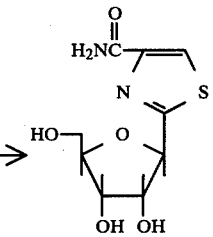

2-β-D-ribofuranosyl-thiazole-4-carboxamide

Where: Ac = —CCH₃   Bz = —C(C₆H₅)

(Ac = $-\overset{O}{\underset{\|}{C}}CH_3$, Bz = $-\overset{O}{\underset{\|}{C}}C_6H_5$)

Certain advantages which are reflected in this process are set out as follows:

1. Preparation of sugar cyanide (II): The explosion and flammability hazard using CH₃NO₂ was eliminated by using methylene chloride.

2. Preparation of thioamide (III): The literature method [Srivastava, et al, J. Med. Chem., 20, 256 (1977)] used the highly toxic liquid H₂S as a solvent requiring the application of an autoclave. This was eliminated by the process development permitting the use of an equimolar amount of H₂S in ethanol.

3. Preparation of thioamide (III): The literature (Srivastava, et al, supra) isolated the thioamide as an impure, unwieldy foam. This improved method permits product isolation directly from the reaction medium as a solid, crystalline thioamide of high purity.

4. Preparation of thiazole ester (IV): A sterospecific synthesis was made possible by the concept that acid formation during the thiazole formation opened the furanose ring producing mixtures of the undesired α- anomer and the desired β-anomer. This problem was solved by using an acid acceptor causing complete retention of the β-anomer configuration.

5. The problem of β-anomer retention was solved by the suggestion using the resin Dowex 50W-X8, sodium form as the acid acceptor.

6. Methyl ester thiazole with deblocked sugar: The literature method (Srivastava, et al, supra) deblocked the sugar and formed the target amide in one step. This liberated benzamide, a side-product, which could only be removed by a laborious and expensive chromatography step. The discovery was made that forming an intermediate deblocked methyl ester, the resulting impurity, methyl benzoate could be removed by a simple extraction.

7. Conversion of the methyl ester to the target thiazole amide: The literature method (Srivastava, et al, supra), leading to the formation of the thiazole amide, produced an oil which could only be purified to the desired crystalline material by an expensive chromatography manipulation. The discoveryt was made that the problem was caused by the formation of the impurity 1-ribosecarboxamide. The concentration was 7–10%.

8. The problem of #7 above was solved by operating the amidation reaction at a much lower temperature; that is, 0° C. Formation of the impurity was minimized permitting the isolation of the desired material as a crystalline product.

Prior Art Statement

Srivastava, et al, "Synthesis and Antiviral Activity of Certain Thiazole C-Nucleosides," *J. Med. Chem.*, 20, 256 (1977) itemizes the synthesis of 2-β-D-ribofuranosylthiazole-4-carboxamide and illustrates that this thiazole nucleoside was active against type 1 herpes virus, type 3 parainfluenza virus, and type 13 rhinovirus and an in vivo experiment run against parainfluenza virus. The process set out in this journal article represents the state of the art from which the present process was generated.

Related art of 1,2,4-triazole nucleosides are:
U.S. Pat. No. 3,798,209 Witkowski et al
U.S. Pat. No. 3,897,415 Robins et al
U.S. Pat. No. 3,927,216 Witkowski et al
U.S. Pat. No. 3,976,545 Witkowski et al
U.S. Pat. No. 4,138,547 Christensen et al
U.S. Pat. No. 4,211,771 Witkowski et al
U.S. Pat. No. Re. 29,835 Witkowski et al

EXAMPLE 1

2,3,5-Tri-O-benzoyl-D-ribofuranosyl bromide (I)

Dry HBr (dried by passing it through a sulfuric acid trap) was passed through a cold (5°), stirred suspension of tri-O-benzoyl-α-acetyl-D-ribofuranose (1.00 kg; 1.98 mol) in dry toluene (6.50 L) (toluene was dried over 4 A molecular sieves) for 2.5 hours. The resulting orange solution was removed from its ice bath, then stirred for an additional 30 min. The reaction mixture was concentrated in vacuo at 32°–35° to an oil, then co-distilled in vacuo at 32°–35° with dry toluene (1.2 L). This material was dried in vacuo at room temperature to give the bromo-sugar as a gum which was used immediately for further transformation.

EXAMPLE 2

2,3,5-Tri-O-benzoyl-β-D-ribofuranosyl cyanide (II)

A suspension of 2,3,5-tri-O-benzoyl-D-ribofuranosyl bromide (I) (1.98 mol) and dry Hg(CN)$_2$ (750 g; 2.97 mol) (mercury (II) cyanide was dried in vacuo at 140° for 12 hours) in dry CH$_2$Cl$_2$ (10.0 L), was stirred for 16 h at room temperature protected from moisture. The insolubles were collected and discarded. The filtrate was washed in succession with 5% aqueous KI (2×6.0 L) and water (2×6.0 L), dried over Na$_2$SO$_4$ (1.0 kg) and charcoal (35 g), then concentrated in vacuo to an oil. This material was diluted with EtOH (2.0 L) then concentrated in vacuo to an oil. The oil was slowly added to petroleum ether (bp, 63°–75°)-EtOH (21.0 L; 7.0 L) with vigorous stirring. The oil slowly solidified, and after 3 h of stirring, the resulting solid was collected and washed with petroleum ether (bp, 63°–75°) (1.0 L). This material was washed by resuspension (17 h) in EtOH (1.50 L). The off-white colored solid was collected, washed with petroleum ether (bp, 63°–75°) (2×500 ml) then dried to constant weight in vacuo to give 598 g (64°) of product; mp, 77.5°–79°. Additional reactions were carried out to give a total of 4894 g of product suitable for further transformation.

EXAMPLE 3

2,5-Anhydro-3,4,6-tri-O-benzoyl-D-allonthioamide (III)

H$_2$S was passed through a stirred suspension (20°–22°) of 2,3,5-tri-O-benzoyl-β-D-ribofuranosyl cyanide (900 g; 1.91 mol) in EtOH (9.4 L) for 5 min, then a solution of 4-N,N-dimethylaminopyridine (18.1 g; 0.148 mol) in EtOH (360 ml) was added in one portion. H$_2$S was passed through the stirred reaction mixture for an additional 3.5 h. The mixture was stirred 15.5 h at room temperature, flushed with argon (30 min), acidified with concentrated HCl (43.5 ml) in EtOH (360 ml), then clarified by filtration. The filtrate was concentrated in vacuo to a yellow foam. This material was dissolved in CH$_2$Cl$_2$ (10.0 L), and the solution was washed with water (2×10.0 L). The organic layer was dried over Na$_2$SO$_4$ (150 g), decolorized (charcoal), then concentrated in vacuo to give 919 g (95%) of product as a yellow foam. Additional reactions were carried out to give a total of 4887 g of product which was combined with a quantity of previously synthesized material to give 5086 g of material suitable for further transformation.

Isolation of crystalline thioamide. Hydrogen sulfide was passed through a cold (8°–10°) stirred suspension of 2,3,5-tri-O-benzoyl-β-D-ribofuranosyl cyanide (110 g; 0.233 mol) in EtOH (1.2 L) for 5 min, then a solution of 4-dimethylaminopyridine (2.2 g; 0.0164 mol) in EtOH (40 ml) was added in one portion. Hydrogen sulfide was slowly passed through the stirred reaction mixture for 5 h. The flask was sealed, and stirring was continued (8°–12°) for 16 h. Argon was passed through the reaction mixture for 1 h to remove last traces of H$_2$S. The suspension was cooled to 0°–3° then separated by filtration. The solid was washed with cold EtOH (150 ml), then dried to constant weight in vacuo to give 108.3 g (92%) of purified product, mp 131°–133°. TLC Data: The compound moves as one major spot and trace front running impurity on silica gel developed with EtOAc/CHCl$_3$ (1:9). NMR and IR spectra support the assigned structure.

This modification offers the following advantages in scale up. First, evaporation to a foam, which fills the evaporator, is eliminated. Second, additional purification is achieved compared to previous method as seen by enrichment of impurities in filtrate. Third, a considerable savings in labor and materials is realized by this modification.

EXAMPLE 4

Thiazole-4-carboxylic acid, 2-(2',3',5'-tri-O-benzoyl β-D-ribofuranosyl)-, ethyl ester (IV)

To a stirred mixture of 2,5-anhydro-3,4,6-tri-O-benzoyl-D-allonthioamide (1.80 kg; 3.56 mol) and Dowex 50W-X8, Na30 cation exchange resin (1.8 L) in EtOH (18.0 L) was added ethyl bromopyruvate (3.85 mol) in one portion. [Commercial technical grade ethyl bromopyruvate (2220 g) was distilled at reduced pressure (10 mm Hg). The material distilling at 90°–97° was collected to give 1754 g (79.0% recovery) of purified material.] The resulting mixture was stirred at 40° for 24 h, allowed to stand at room temperature for 36 h, then stirred for an additional 8 h at 40°. Since unreacted 2,5-anhydro-3,4,6-tri-O-benzoyl-D-allonthioamide was present, as determined by tlc, an additional portion of ethyl bromopyruvate (0.072 mol) was added to the reaction mixture which was stirred for an additional 18 h at 40° to insure complete reaction. The cation exchange resin was removed by filtration and washed with EtOH (500 ml). The combined filtrate and washing were concentrated in vacuo to give the crude product as 2785 g of a deep brown syrup. Additional reactions were performed to give a total of 6166 g of this material. 5771 g of this syrup was directly chromatographed on 18×3.5 kg silica gel wet columns packed in and developed with EtOAc-CHCl$_3$ (1:9). The portions containing the β-isomer, as determined by tlc, were combined and concentrated in vacuo (30°–35°) to give 3103 g of partially purified product as a hard brown oil suitable for further transformation.

EXAMPLE 5

2-β-D-Ribofuranosylthiazole-4-carboxylic acid, methyl ester (V)

To a stirred (5°) solution of NaOMe (73.8 g; 1.37 mol) in dry MeOH (8.0 L) was added thiazole-4-carboxylic acid, 2-(2',3',5'-tri-O-benzoyl-β-D-ribofuranosyl)-, ethyl ester (IV) (777 g; 1.29 mol) in dry MeOH (8.0 L) during 5 min. The reaction mixture was stirred at room temperature for 16 h, neutralized with Dowex 50W-X8, H+ resin [6 lbs, previously wshed with dry MeOH (5×3 L)], then spin-evaporated in vacuo (30°–35°) to an oily residue. This material was paretitioned between water (4 L) and CHCl$_3$ (1.5 L). The aqueous layer was separated, washed with CHCl$_3$ (7$^3$×1.5 L) to remove last traces of methylbenzoate, decolorized (charcoal) then spin-evaporated in vacuo (30°–35°) to an oil. The oil was co-distilled in vacuo (30°–35°) with EtOH (150 ml) to give a pale green solid which was dried to constant weight in vacuo over P$_2$O$_5$ to give 261 g (73%) of product. Additional reactions were performed to give a total of 760 g of this material which was chromatographed on 7×3.5 kg silica gel wet columns packed in EtOAc and developed with EtOAc-1-PrOH-H$_2$O (3:2:1). The portions containing pure material, as determined by tlc, were combined and concentrated in vacuo to give a white solid which was co-distilled in vacuo with a small amount of EtOH to give 513 g (68% recovery) of material. A 12.6 g sample of this chromatographed material was vigorously triturated in Et$_2$O (100 ml), recovered by filtration, and dried to constant weight in vacuo at 50° over P$_2$O$_5$ to give 11.8 g (94% recovery) of analytically pure product. The trituration of 481 g of the remaining chromatographed material in Et$_2$O (7.5 L) yielded 452 g of material which was combined with 150 g of material obtained in a similar fashion to give 602 g of product suitable for further transformation.

| Anal. | C | H | N | O | S |
|---|---|---|---|---|---|
| Calc'd. for C$_{10}$H$_{13}$NO$_6$S | 43.63 | 4.76 | 5.09 | 34.87 | 11.65 |
| Found | 43.65 | 4.80 | 4.97 | 34.71 | 11.51 |

Spectral Data

Infrared (Melt): Major bands: 3400, 2920, 1720, 1480, 1430, 1330, 1220, 1090, 1035, 975, 850, 740 cm$^{-1}$.

Ultraviolet (H$_2$O): $\lambda_{max}$ 205 nm (log=4.22); 239 nm (3.88).

Nuclear Magnetic Resonance (DMSO-d$_6$) δ8.50 (s, 1H, H at C-5); 5.60–4.80 (m, 3H, —OH); 5.00 (d, 1H, J=4 Hz, αH at C-1'); 4.30–3.35 (m, 5H, —CH$_2$— and H at C-2', C-3', C-4'); 3.85 (s, 3H, —OCH$_3$).

Optical Rotation: $[\alpha]_D^{20}$ −17.4° (C, 1.1 in DMF).

Chromatography

| Thin Layer Chromatography (Silica Gel, E. Merck 60 F-254 Glass Plates) | |
|---|---|
| Solvent System | R$_f$ Value |
| 1. EtOAc-1-PrOH-H$_2$O (3:1:2)* | 0.60 |
| 2. EtOAc-1-PrOH-H$_2$O (4:1:2)* | 0.45 |
| 3. EtOAc-1-PrOH-H$_2$O (3:2:1) | 0.60 |

*Mixture was allowed to saturate; top layer was used.
Detection: Ultraviolet light
Quantity spotted: 90 μg
Results: The compound moves as a single spot in each solvent system.

EXAMPLE 6

Dry MeOH (6.2 L) was saturated (with stirring at 0°) with NH$_3$ during 4 h. 2-β-D-ribofuranosylthiazole, 4-methyl ester (390 g; 1.42 mol) was dissolved in the cold (5°), NH$_3$/MeOH solution, then the flask was sealed and stored at 0°–3° for 72 h. The reaction mixture was concentrated in vacuo at 30° to a foam which was triturated in warm (40°) abs EtOH (1.8 L) to give 291 g (79%) of product; mp 120°–123°. The EtOH filtrate was separated by HPLC in EtOAc/n-PrOH/H$_2$O (4:1:2; top layer) to give an additional 67 g of similar material for a total yield of 97%. Additional material (57.1 g) from development work was combined to give a total of 414.1 g of product which was recrystallized from abs EtOH (2.9 L) to give 343.7 g (83% recovery) of purified product. An additional reaction was carried out to give a total of 433 g of purified material; mp 142°–143°.

| Anal. | C | H | N | O | S |
|---|---|---|---|---|---|
| Calc'd. for C$_9$H$_{12}$N$_2$O$_5$S | 41.53 | 4.65 | 10.76 | 30.74 | 12.32 |
| Found | 41.64 | 4.70 | 10.63 | 30.59 | 12.24 |

Spectral Data

Infrared (Nujol): Major bands: 3540, 3460–3100, 2950, 2860, 1660, 1600, 1520, 1450, 1375, 1300, 1240, 1210, 1180, 1080, 1050, 1030, 980, 945, 870, 845, 780 cm$^{-1}$.

Ultraviolet (0.5% aqueous Na$_2$CO$_3$; pH 11): $\lambda_{max}$ 239 nm ($\epsilon$ 7365) log $\epsilon$ 3.867.

Nuclear Magnetic Resonance (DMSO-d$_6$): $\delta$8.27 (s, 1H, thiazole ring H); 7.65 (d, 2H, J=8 Hz, —NH$_2$); 5.50–4.70 (m, 4H, —OH and H at C-1); 4.40–3.50 (m, 5H, H at C-2, C-3, C-4, and C-5). The spectra shows the presence of ~1% EtOH.

Optical Rotation. Observed: $[\alpha]_D^{20}$ −13.2° (c, 0.11, DMF).

Chromatography

| Thin Layer Chromatography (Silica Gel, E. Merck 60 F-254 Glass Plates) | |
|---|---|
| Solvent System | R$_f$ Value |
| 1. EtOAc/n-PrOH/H$_2$O (4:1:2) (2-phase system was stirred, then the top layer was used) | 0.35 |
| 2. EtOAc/n-PrOH/H$_2$O (3:2:1) | 0.55 |

Detection: Ultraviolet light and H$_2$SO$_4$ spray
Quantity Spotted: 125 and 250 μg
Results: The compound moves as a single spot in each system. A faint spot detectable by H$_2$SO$_4$ is observed in each system just below the main spot. This material was isolated, characterized, then tentatively identified as being 1-ribosecarboxamide. Comparative quantitative TLC indicates the impurity is present in a quantity of 1% or less.

We claim:

1. A multi-step process for the production of 2-β-D-ribofuranosylthiazole-4-carboxamide (NSC-D286193) utilizing the following steps:

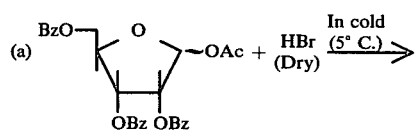

Tri-O—benzoyl-α-acetyl-D-ribofuranose

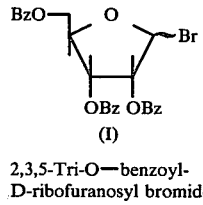

(I)

2,3,5-Tri-O—benzoyl-D-ribofuranosyl bromide

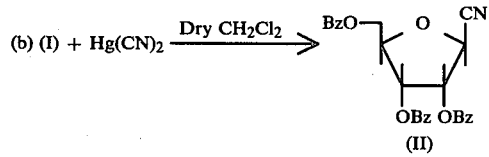

(II)

2,3,5-Tri-O—benzoyl-β-D-ribofuranosyl cyanide

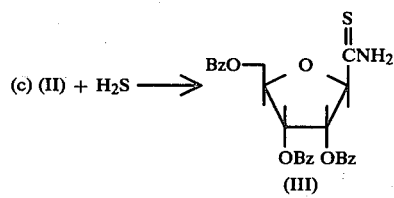

(III)

2,5-Anhydro-3,4,6-tri-O—benzoyl-D-allonthioamide

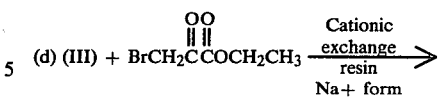

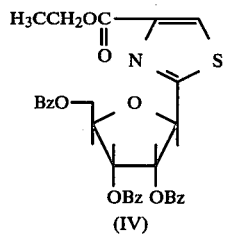

(IV)

Thiazole-4-carboxylic acid, 2-(2′,3′,5′-tri-O—benzoyl-β-D-ribofuranosyl)-, ethyl ester

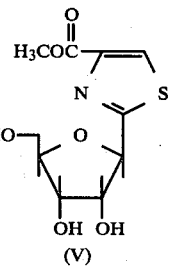

(e) (IV) + NaOMe ⟶

(V)

2-β-D-ribofuranosylthiazole-4-carboxylic acid, methyl ester

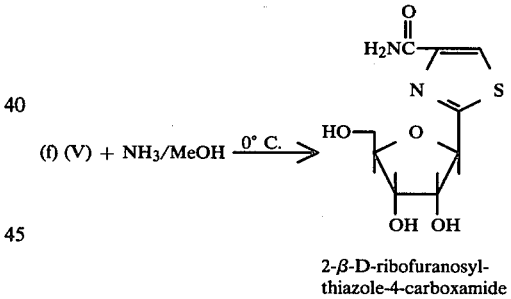

2-β-D-ribofuranosyl-thiazole-4-carboxamide

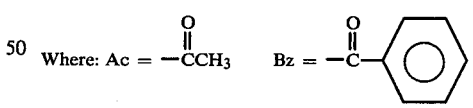

2. The process according to claim 1 step (b) wherein the preparation of sugar cyanide (II) utilizes as a solvent methylene chloride.

3. The process according to claim 1 step (c) wherein the preparation of thioamide (III) utilizes equimolar H$_2$S in ethanol.

4. The process according to claim 1 step (c) wherein in the preparation of thioamide, the preparation of an isolation of the thioamide as a solid crystalline high purity product.

5. The process of claim 1 step (d) wherein bromopyruvate is added to stabilize the ring formation of the furanose ring consolidating production of the β-anomer together with a cationic exchange resin as the acid acceptor.

6. The process according to claim 1 step (e) wherein the intermediate product 2-β-D-ribofuranosylthiazole-4-carboxylic acid, methyl ester (V) is prepared as an intermediate deblocked sugar.

7. The process according to claim 1 step (f) wherein the amidation reaction is carried out at an unusually low temperature of about 0° C. permitting isolation of a crystalline product.

8. The compound 2-β-D-ribofuranosylthiazole-4-carboxylic acid, methyl ester.

* * * * *